United States Patent [19]

Sugaar

[11] 4,343,895

[45] Aug. 10, 1982

[54] ENCAPSULATED ANTIGENIC TUMOR SPECIFIC SUBSTANCES AND METHODS FOR DETECTING CANCER USING SAID SUBSTANCES

[76] Inventor: Stephen Sugaar, 21 Louis St., Staten Island, N.Y. 10304

[21] Appl. No.: 152,535

[22] Filed: May 23, 1980

[51] Int. Cl.$^3$ .................. C12Q 1/68; G01N 33/54
[52] U.S. Cl. ................................ 435/6; 435/7; 23/230 B; 424/12
[58] Field of Search .......... 435/7, 6; 23/230 B; 424/7, 8, 12; 252/408 R

[56] References Cited

U.S. PATENT DOCUMENTS

| | | | |
|---|---|---|---|
| 3,999,944 | 12/1976 | Grosser et al. | 424/12 |
| 4,193,983 | 3/1980 | Ullman et al. | 435/7 |

OTHER PUBLICATIONS

Sakai F. et al.; "Association of Gross Virus-Associated Cell-Surface Antigen with Liposomes"; Br. J. Cancer, vol. 41, pp. 227-235 (1980).
Gerlier D., et al., Induction of Antibody Response to Lipsome-Associated Gross-Virus Cell-Surface Antigen (GCSAa); Br. J. Cancer, vol. 41, pp. 236-242 (1980).
Willoughby E. M. et al.; "Incorporation of Rat Histocompatibility (AgB) Antigens into Liposomes, and their Susceptibility to Immune Lysis"; Eur. J. Imm. 1978,8, 628-634.
Kahan B. D. et al.; "Purification of Tumor-Specific Antigens"; Cancer, December Suppl. 1975; vol. 36, pp. 2449-2454.
Wahlström, T. et al., "Tumor-Specific Membrane Antigens in Established Cell Lines from Gliomas"; Cancer, vol. 34, pp. 274-279 (1974).
Currie, "Immunological . . . Cancer," Biochimica et Biophysica Acta 458 (1976), pp. 135, 154, 155.
Galindo et al., "Fusion . . . Antigen," Infection and Immunity, vol. 9 (1974), pp. 212-216.
Poste et al., "Lipid . . . Cells," Proc. Natl. Acad. Sci. USA, vol. 73 (1976), pp. 1603-1607.
Ramey et al., "Detection . . . Formation", Cancer Research, vol. 39 (1979), pp. 4796-4801.
Riley et al., "Neoplastic . . . Irradiation", Abstract OS2-/7-2 of International Union of Radio Science XIX General Assembly, Helsinki, Finland (1978).
Sone et al., "Rat . . . Lymphokines," The Journal of Immunology, vol. 124 (1980), pp. 2197-2202.
Suit et al., "Immunogenicity . . . Heat," Cancer Research, vol. 37 (1977), pp. 3836-3837.
Warfel, "Macrophage . . . Morphology," Experimental and Molecular Pathology, vol. 28 (1978), pp. 163-176.

*Primary Examiner*—Benoit Castel
*Attorney, Agent, or Firm*—Frishauf, Holtz, Goodman & Woodward

[57] ABSTRACT

The present invention provides encapsulated antigenic tumor-specific substances prepared by extracting said antigenic tumor-specific substances in an aqueous phase and then encapsulating said aqueous phase. Said encapsulated substances are characterized by a degree of antigenic activity such that when they are contacted with a composition of naturally tumor-sensitized lymphocytes taken from a host having cancer in the presence of macrophages, macrophage fusion occurs to form at least one multinucleated giant macrophage cell. The invention further provides diagnostic tests for the determination of cancer which utilize said strongly antigenic tumor-specific substances as reagents.

3 Claims, No Drawings

ENCAPSULATED ANTIGENIC TUMOR SPECIFIC SUBSTANCES AND METHODS FOR DETECTING CANCER USING SAID SUBSTANCES

BACKGROUND OF THE INVENTION

The present invention provides a method for the preparation of novel compositions containing strongly antigenic tumor-specific substances and cancer diagnostic methods utilizing said substances and compositions.

It is known that several human cancers such as melanomas, breast or colon cancer possess weakly antigenic tumor-specific substances on the membranes of their composing tumor cells. With the usual methods for extraction and ultracentrifugation, these tumor-specific antigens sometimes referred to in the literature as TSTA's and herein referred to as "TSAs," prove to be even weaker antigens than when in their native association with malignant tumor cells, see K. Sikora et al's article "Purification of Tumor-Specific Transplantation Antigens from Methylcholantrene-Induced Murine Sarcomas by Immobilized Lectins," British J. Cancer 40:831–838, (1979). There is a recent report on sensitization of circulating lymphocytes of women with breast cancers to breast cancer TSAs, see Wm. G. Ramey et al.'s article "Detection of Breast-Tumor Antigen-Sensitive Circulating T-Lymphocytes by Antigen-Stimulated Active Rosette Formation," Cancer Research 39:4796–4801, (1979). This effect may be due to persistent release of breast TSAs of weak antigenicity into the circulation, see G. Currie's "Immunological Aspects of Host Resistance to the Development and Growth of Cancer," Biochimica & Biophys. Acta 458: pp. 154–155, 1976. Because of the weak antigenicity of known TSAs, it has not been possible to establish reliable diagnostic tests for cancer using the TSAs, nor has it been possible to develop therapeutic means utilizing TSAs.

It is known that when lymphocytes sensitized by strong antigens, e.g. Bacillus Calmette-Guerin (BCG), on recontacting the strong sensitizing antigen in vivo or in vitro, macrophages present at the site of reaction may fuse and form multinucleated giant cells, see A. H. Warfel's article "Macrophage Fusion and Multinucleated Giant Cell Formation, Surface Morphology," Experimental & Molecular Pathology 28:163–176 (1978). TSAs obtained from cancer cells are, as noted, weak antigens and when such weak TSAs are contacted with lymphocytes in the presence of macrophages, no macrophage fusion reaction occurs in vivo or in vitro. Conventional heat treatments have been reported to raise to some degree the inherently weak immunogenicity of tumor cells, but the immunologic change was found to be inferior to that produced by X-rays., see H. D. Suit et al.'s article "Immunogenicity of Tumor Cells Inactivated by Heat," Cancer Research 37:3836–3837 (1977). TSAs after conventional heating, while somewhat more active than TSAs produced without heating, are not sufficiently activated to produce specific histologic or in vitro reactions such as the macrophage fusion reaction.

All publications referred to are incorporated herein by this reference.

It is an object of the invention to produce compositions containing TSAs having strong antigenic activity and further to utilize such strongly antigenic TSAs in methods for testing for cancer, and for therapeutic uses.

SUMMARY OF THE INVENTION

The encapsulated antigenic TSAs are obtained by extracting from cancer tissue or aggregates cancer cells, or cancer cell membranes into an aqueous phase which is a physiologic solution, preferably a tissue culture medium. Preferably small amounts of anti-protease are added to prevent possible decomposing action from native proteases exuding from tumor cells. The extracted material may be heated to temperatures of about 42° C. and above.

TSAs are preferably extracted from the cancer cell material using various extraction techniques. It is preferred to utilize a mild detergent in a buffer. The detergent content of the TSA extract is then removed by dialysis and the extract is filtered through ultrafiltration membranes to obtain a final concentrate from which anti-protease, excess water, salts and other substances of less than 40,000 and more than 300,000 dalton molecular weight are removed leaving the strongly antigenic TSAs with molecular weights between about 40,000 to 300,000 dalton in water in the form of a very fine non-settling suspension. The molecular weight is preferably between about 50,000 and 80,000 dalton. The extracted substances also contain histocompatible antigen (HLA) which, like the TSAs, are (i) derived from the membranes of tumor cells and (ii) contain in non-covalent binding beta-2-microglobulin. The TSA extracts containing compositions of the present invention may be utilized when they contain the aforesaid HLAs and their bound beta-2-microglobulin, or the HLAs may be removed as disclosed hereinafter.

The TSA extracts are encapsulated into multilamellar liposome vesicles to increase the natural native low antigenic power of TSAs. The encapsulation is preferably carried out by a modification of Poste's method disclosed in G. Poste et al.'s article "Lipid Vesicles as a Carrier for Introducing Materials into Cultured Cells: Influence of Vesicle Lipid Composition on Mechanism(s) of Vesicle Incorporation into Cells," Proc. Nat'l. Acad. Sci., 73:1603 (1976).

TSAs encapsulated according to the present invention are evidenced by their ability when contacted with native sensitized lymphocytes obtained from cancer patients and in the presence of ambient (nearby) macrophages to cause macrophage fusion. Although the macrophage fusion test is utilized to establish that the strongly antigenic TSAs have been produced, the strongly antigenic TSAs have other utility than solely for use in the macrophage fusion of the test. They may be used in other tests to determine the presence of cancer; for example, with the cytofluorometric test discussed hereinafter. They may also have therapeutic utility, e.g., in the extracorporeal or parenteral stimulation of mononuclear cells of cancer patients.

The encapsulated strongly antigenic TSAs can be utilized in a macrophage fusion test to determine whether a lymphocyte-containing peripheral blood sample contains cancer sensitized lymphocytes which would indicate that the person or animal from whom they were obtained suffers or suffered from cancer. The test is analogous to the test reported by B. Galindo et al., "Fusion of Normal Rabbit Alveolar Macrophages Induced by Supernatant Fluids from BCG-Sensitized Lymph Node Cells After Elicitation by Antigen," Infection and Immunity, 9:212–216 (1974), who first used such tests with non-tumor derived strong sensitizer substances such as BCG or Nocardia brasiliensis antigens. The results of this test are established by counting the fused macrophages and multicellular giant cell formations visible on microscopic examination. Percentual terms reflecting the decrease in single macrophages and increase in the numbers of fused macrophages in culture chambers respective of starting and final cell counts are compared.

It is known that blastogenic changes can result when lymphocytes of sensitized persons recontact the sensitizer antigen or antigens. Simulation response curves obtained with TSA stimulated patient's lymphocytes provide on cytofluorometric analysis quantitative data reflecting DNA/RNA ratio alterations of diagnostic significance. Cancers other than gastrointestinal or liver cancers may contain antigens such as carcinoembryonic antigen (CEA). It should be considered to remove CEA from TSA extracts by passing such through anti-CEA treated absorbent columns, particularly if non-specific reactions are encountered with gastrointestinal or liver TSAs acting on lung cancer-sensitized lymphocytes.

Extracted TSAs in aqueous non-settling suspension interspersed between the lamellae of liposomes are the preferred form of the strong antigenic tumor-derived substance of the present invention. Although the compositions containing the extracted TSAs are preferred, it is possible to utilize the tumor cell material or the tumor cell membranes as disclosed herein without extracting the TSAs from native cellular source as an antigen substance alternate to the extracted TSAs as the material to be encapsulated and used as a reagent in the diagnostic tests and therapeutic uses contemplated.

DETAILED DESCRIPTION OF THE INVENTION

Preparation of Soluble Cancer-Associated Tumor-Specific Antigens (TSAs)

Surgically excised, aseptically handled solid cancer tissue, or such obtained from autopsied organs, should be freed from attached fatty tissue, connective tissue and visible necrotic tumor tissue and blood. 1 vol. of tumor tissue is placed in containers with 2 vols. buffered saline containing 0.1 mM phenylmethyl-sulfonyl-fluoride (PMSF) to prevent autologous tissue proteases to damage TSAs. The suspended or immersed wet tumor tissue is cut with scalpel and scissors and the tumor particles are strained through a 40 mesh metal screen. The finely dispersed tumor particles are suspended in 15 vols. MRPI-1650 tissue culture medium at pH 7.7, containing 0.1 mM PMSF and are enclosed in a chemically inert plastic container.

Alternately, the cancer cell membranes may be removed from the tumor cells using the procedure disclosed in Anneliese Wolf's article "The Activity Of Cell-Free Tumour Fractions In Inducing Immunity Across A Weak Histocompatibility Barrier," Transplantation, Vol. 7, No. 1, pages 49–58 (1969), and then treated in place of the carrier tissue as aforedisclosed.

HEATING OF MALIGNANT TUMOR TISSUE

The immunogenic power of some heated experimental animal tumors was found to be increased over that of their non-heated counterparts according to D. H. Suit et al. who used 43.5° C. heating for 240 minutes ("Immunogenicity of Tumor Cells Inactivated by Heat," Cancer Research, 37:3836–3837, 1977); and according to J. H. Check et al. who used a 65° C. heating period for 30 minutes ("Protection Against Spontaneous Mouse Mammary Adenocarcinoma by Innoculation of Heat-treated Syngeneic Mammary Tumor Cells," International J. of Cancer, 7:403–408, 1971). J. H. Check et al. assumed (loc. cit. p. 407) "that partial denaturation of the proteins by heat treatment altered the TSTA in such a way as to allow the animal to immunologically respond to the modified antigen."

For the intents and purposes of this invention, both non-heated and/or heated tumor or tumor derived TSA containing antigenic material are usable in watery medium (e.g. MRPI-1640 tissue culture medium) to form the aqueous component enclosed between the lipid lamellae of liposomes.

Heating of human or animal tumor tissue, cell or all membrane extract including isolated TSA extracts should be between 41° and 100° C. preferably between 42.5° and 46° C., the time period of heating being between 30 and 180 minutes, preferably between 45 and 120 minutes.

The tumor tissue or tumor derived materials suspended or immersed in the liquid medium are heated in a chemically inert firmly plugged plastic container as aforesaid.

Extraction of the Antigen (TSAs)

The tumor cells or the tumor cell membrane preparation, after the heating stage, suspended in buffer are added with 10× volume of the buffered solution at pH 7.7 containing 0.1 mM, PMSF and lithium diiodosalicylate (0.01 to 0.5 M) or other detergents such as 0.5% deoxycholate and Triton-X100 (0.1–1% w/v). The tumor derived suspension is then agitated for 15 minutes at a slow rate or by mild sonication at room temperature. Any gross tumor particles present are allowed to sediment, the supernate is removed and centrifuged at 1000× g for 15 minutes at 40° C.—the cell-free supernate of the centrifugate is dialyzed in Visking tubing 8-1/32 at 4° C. with three changes of dialysate for 48 hours. The dialysate is passed through Diaflo Ultrafilter UM-10 (Amicon Corp., Lexington, Mass.). Filtration pressure preferably should not exceed 110 psi.

The retained dehydrated, desalted fluid is diluted with 20× buffer and filtered through Diaflo Ultrafilter XM-50 at 60 psi pressure.

The retained fluid is passed through Diaflo Ultrafilter XM-300 at 20 psi pressure; the fluid passing through the filter is collected and identified as TSA test extract. The extracts molecular weight is within 40,000 to 300,000 daltons and it contains strongly antigenic TSAs as well as LHAs. Some aliquots of the TSA extracts are scheduled for the diagnostic tests proper, other aliquots are preserved in a frozen condition (−70° C.) or after lyophilization for later use. Higher concentrations of TSA test extracts may be obtained by the hollow-fiber concentration method (Bio-Rad Lab., Richmond, Calif.).

Alternately, the tumor cell material may have the TSAs extracted therefrom using the Reisfeld and Kahan method wherein 3 M KCl hypertonic salt is slowly added to the cell suspension for a 30-min. period to reach a final concentration of 3 M. The extraction mixture is incubated at 4° C. for 16 hr. with constant stirring. Insoluble cell constituents are sedimented by ultracentrifugation at 164,000×G for 60 min. The supernatant containing solubilized TSAs are concentrated by dialysis against 50% sucrose solution, and then dialyzed against 200 volumes of 0.15 M saline for 16 hr. Precipitates formed during concentration and dialysis were removed by centrifugation at 48,000×G, see Fed. Proc., Vol. 29, page 2034 (1970).

The HLAs may be removed from the crude TSA extracts. Initially, the KBr flotation method of Reisfeld et al., disclosed in the article "HL-Antigens in Serum and Urine: Isolation, Characterization and Immunogenic Properties," TRANSPLANTATION PROCEEDINGS, Vol. 8; pages 173-178 (1976), was used for removal Of HLA antigens from TSA extract. The specific density of the KBr solution (1.22) is determined by pyknometry. Five ml of the KBr solution is added to each three 15-×60-mm cellulose nitrate ultracentrifuge tubes (Beckman Instruments, Palo Alto, Calif.), and 0.1 ml of TSA extract is carefully layered on top of the KBr solution. Each tube is placed in a SW50 rotor and run in a Spinco preparative ultracentrifuge at 131,000×g for 24 hr. Upon completion, 3 phases (upper, interphase, and lower) are withdrawn from the centrifuge tubes with a peristaltic pump (LKB PERPEX; KLB Western Instruments, Inc., Pleasant Hill, Calif.) fitted with a fine capillary tube. The upper phase, which contains HLA antigen activity, does not possess TSA activity. The lower phase, which contains no HLA activity, has essentially all the TSA activity present.

Methods & Materials for Preparation of Liposomes Containing TSA

Lipid spherules referred to as liposomes have been known as carriers for aqueous interphased watery materials since their initial description by A. D. Bangham et al: "Diffusion of Univalent Ions Across the Lamellae of Swollen Phospholipids," Journal of Molecular Biology, 13:238-252 (1965). More recent disclosures of encapsulation in liposomes are contained in papers by W. E. Magee et al.: "The Interaction of Cationic Liposomes Containing Entrapped Horseradish Peroxydase With Cells in Culture," Journal of Cell. Biology, 63:492-504 (1974), And S. Sone et al.: "Rat Alveolar Macrophages Are Susceptible to Activation by Free and Liposome-Encapsulated Lymphokines," Journal of Immunology, 124:2197-2002 (1980).

Liposome particles of the present invention are prepared by the dispersion of dried films of phospholipids in an aqueous phase and materials such as the TSAs which are contained in the aqueous phase become trapped between the bilayer lamellae of the lipid particles.

Sphingomyelin liposomes were prepared by dissolving 50 mg of sphingomyelin (highly purified, from bovine brain), 10 mg cholesterol, and 6 mg stearylamine in 18 ml chloroform together with a small amount of methanol. The solution was divided among six 50-ml round-bottom flasks or three 100-ml round-bottom flasks, and the solvent was removed by flash evaporation on a rotary evaporator at room temperature. The flasks were flushed with $N_2$ and 0.3-0.5 ml of the aqueous suspension containing the extracted TSAs was added per flask.

An alternate method for preparing liposomes is taking egg phosphatidylcholine, beef brain phosphatidylserine and lysolecithin at mole ratios 4.95:4.95:0.01, respectively, in a total weight of 66 mg. This is dissolved in 18 ml chloroform together with a small amount of methanol. The solution is divided among six 50-ml round-bottom flasks and the solvent evaporated, the flasks flushed with $N_2$ and the aqueous phase containing TSAs added in 0.3-0.5 ml quantities to individual flasks. The aqueous phase contained the TSAs which included in non-covalent binding as a part of the macromolecule, beta-2-microglobulin in 0.1 M phosphate buffer, pH 6.9; the 0.3-0.5 ml TSAs in aqueous phase containing not less than 5,000 and not more than 25,000 nanograms beta-2-microglobulin in non-covalent binding with the TSAs.

The films were dislodged from the glass by the use of a Vortex-Genie mixer. Two or three glass beads may be added to aid in loosening the lipid film. The liposomes are removed from the flasks, and the flasks rinsed with a small amount of aqueous phase. The liposomes are treated with ultrasonic vibration in intermittent 20-s intervals at 4°-10° C. for a total of 1-2 minutes with a Branson Biosonic III vibrator equipped with a microprobe. The preparation is diluted with a saline-phosphate (0.15 M NaCl and 0.01 M phosphate, pH 6.9) and the liposomes collected by centrifugation at 60,000 g for 30 minutes in the 50 Ti rotor of a Beckman Ultracentrifuge. The pelleted liposomes are resuspended and washed twice more by centrifugation and stored at 0°-5° C. suspended in saline-phosphate for use in variable aliquots in the cancer tests.

Macrophage Fusion Assay

A. The macrophages utilized are pulmonary alveolar macrophages obtained from laboratory animals, preferably from rabbits. The preparation method follows the technical procedure of Q. N. Myrvik et al.'s article "Studies on Pulmonary Alveolar Macrophages from the Normal Rabbit," J. of Immunology 86:123-132 (1961). Normal adult rabbits are sacrificed by injection of 4 ml veterinary Nembutal i.v. The thoracic cavity is opened and the trachea cannulated, introducing 40 ml isotonic tissue culture fluid into the pulmonary bronchial tree. The entry of blood into the operative area is carefully prevented; the culture fluid is withdrawn from the lung and centrifuged at 1500 rpm for 20 minutes; aliquots of the sedimented alveolar macrophages are tested for viability by staining with 0.02% trypan blue solution. Viable macrophages are suspended in MRPI-1640 without serum, washed twice and recovered after centrifugation at 2000×g for 10 min. Macrophage suspensions in culture medium are counted in hemocytometers and their concentration adjusted to $8 \times 10^6$ cells/ml.

B. Lymphocytes of cancer patients and persons being tested for cancer are obtained by venipuncture. 15 ml of heparinized or defibrinated blood is layered on 3 ml commercially available ficoll-hypaque solutions and centrifuged. The mononuclear cells collecting at the interface are collected and washed 3 times with MRPI-1640 culture medium at low centrifugal speeds under sterile conditions. The technique of lymphocyte separation follow Bøyum's method, see A. Bøyum's article, "Isolation of Mononuclear Cells and Granulocytes from Human Blood," Scand. J. Clin. Lab. Invest. 21:77 (1968).

Lymphocyte viability is tested by the trypan blue exclusion method. The washed viable lymphocytes are suspended in RPMI-1640 culture medium containing penicillin-streptomycin (100 units/ml and 100 ug/ml), 20 mM HEPES buffer, cold-preserved l-glutamine (2 mM) and 10% fetal calf serum. The cell count of lymphocytes is set at $1 \times 10^5$ ml culture medium.

The sensitivity of the sensitized lymphocytes to the antigen can be enhanced by treating the lymphocytes with Meuraminidase prior to incubation of the lymphocytes with antigen as described in Tin Han's article "Specific Effect of Neuraminidase on Blastogenic Response of Sensitized Lymphocytes," *Immunology*, 28, pages 283–286 (1975).

For incubation, 0.25 ml aliquots of lymphocytes derived from cancer patients (or known cancer-free donors, resp.) are placed in wells of tissue culture plates (e.g. Limbro tissue culture plates with 12 wells, Flow Labs., Inc., McLean, Va. 0.1 ml liposomes, each liposome containing in its watery phase about 25 microliter TSA extract of previously known quantitated beta-2-microglobulin content is added to 0.2 ml MRPI-1640 medium. The diluted liposome suspension is added in 0.25 ml quantities to each 0.25 lymphocyte aliquot in culture plate wells. All cell cultures are performed in triplicate and are incubated in 5% $CO_2$-95% air atmosphere, humidified to prevent condensation of culture medium and protected from contamination. Incubation should last not less than 24 and not more than 72 hours.

The supernates of lymphocyte cultures are collected and centrifuged at 1000 rpm for 10 minutes at 4° C. Samples of each culture supernate (0.4 ml) are added to 0.1 ml suspensions of rabbit alveolar macrophage cells at concentrations of $1.5 \times 10^6$ alveolar macrophages/ml.

C. The Macrophage fusion assay is carried out using the foregoing materials. Aliquots of macrophage cell suspensions in supernates of incubated lymphocyte cultures are dispensed at 10 microliters per well. Four wells/test are filled on No. 3034 microtest culture plates (Falcon Plastics, Osnard, Calif.). The microtest culture plates are incubated in a $CO_2$ incubator at 37° C. in a humidified atmosphere, under aseptic conditions. Alternately, the lymphocytes response to antigens may be enhanced by culturing at 40° C. as disclosed by the Smith et al article "Human Lymphocyte Responses Are Enhanced By Culture At 40° C.," *The Journal of Immunology*, Vol. 121, No. 2, pages 691–694 (1978). Routinely incubation should be maintained for at least 24 hours (but incubations up to 72 hours should occasionally be employed). Settled macrophages at 1 hour and 24 hours culturing should be photographed at $100\times$ magnification. In positive cultures there are giant cells present at 24 hours incubation at the bottom of the culture wells. The number of single macrophages at 1 hour culturing and at 24 hours as well as the number of giant cells (having nuclei in excess of 5 nuclei per cell) are counted and the respective numbers of single and giant fused macrophage cells as well as the ratios of single/giant cells recorded.

More than 30% giant cells present at 24 hours incubation are considered strongly positive (3+) results. Tests with less than 10% giant cells are considered 1+. Cultures containing 10% to 30% giant cells are considered 2+. However, the presence of even one multinucleated giant cell is a positive finding for cancer, and for strongly antigenic TSAs.

Cytofluorometric Test

The presence of sensitized lymphocytes in the peripheral blood taken from cancer patients can be determined using cytofluorometric analysis and more specifically by flow cytofluorometry the degree of lymphocyte stimulation by tumor TSAs using the simultaneous quantitation of RNA and DNA in test lymphocytes using an Acridine Orange reagent by, e.g., the following method disclosed by Braunstein et al., "Quantitation of Transformed Lymphocytes by Flow Cytofluorimetry," *Federation Proceedings, Vol.* 34, No. 3 (1975), as follows. Liposomes containing TSA will trigger pyroninophilic blastic transformation of cancer sensitized lymphocytes detectable by flow cytofluorimetry and Acridine Orange staining. When TSA containing liposome preparations are used as antigen, each liposome contains in its watery phase preferably about 25 microliter TSA extract of previously known quantitated beta-2-microglobulin content. They are added to TSA responsive and control lymphocyte samples. Lymphocytes separated from anticoagulated human peripheral blood by centrifugation on a Ficoll-Hypaque gradient are incubated at 37° C. or 40° C. in 5% $CO_2$ atmosphere in 5 ml RPMI-1640 containing HEPES buffer and 10% fetal calf serum and l-glutamine (2 mM) at a lymphocyte concentration of 100,000 cells/ml in the presence or absence of 0.1 ml liposomes containing TSAs in their watery phase. The samples are harvested at intervals up to 72 hours, fixed in 1:1 ethanol/acetone and stained with $10^{-5}$ g/ml Acridine Orange in a pH 6 buffer. Cytofluorometric measurements (cytofluorograf 4801 interfaced to a Nova 1220 minicomputer) on replicate samples of stimulated cells show increased per cell red fluorescence. The percentage of transformed cells is determined by quantitating the number of cells with fluorescence intensity falling outside the locus of unstimulated lymphocytes. The percent of stimulated cells increase with time and varies with dose of TSA. Multiple determinations of 10,000 cell samples from single cultures agree within 1%.

The cancer tests disclosed herein indicate whether or not the lymphocytes used in the tests were derived from a host who is currently bearing a malignant tumor or had in the past been afflicted by a cancer.

The cancer diagnostic tests are diagnostic both to site of origin and for the pathohistologic type of cancer under investigation.

Compositions containing the encapsulated strongly antigenic tumor-specific substances may be utilized as materials for extracorporeal or parenteral activation of mononuclear cells of animal or human cancer cases.

I claim:

1. A process for the detection of cancer of defined pathohistological type comprising obtaining a blood or tissue sample of viable lymphocytes from a host, contacting said lymphocyte sample with a liposome composition comprising an encapsulated aqueous phase which contains antigenic tumor-specific substances which comprises antigenic (i) macromolecular tumor-specific substances extracted from cancer cells or separated from cancer cells, or (ii) cancer cell material or membranes separated from cancer cells, characterized by a degree of antigenic activity such that when said composition is (i) contacted with a composition of sensitized lymphocytes taken from a host having cancer of the pathohistologic type as the cancer cells from which the antigenic tumor-specific substances were obtained, and (ii) in the presence of a suspension of macrophage cells prepared from pulmonary alveolar macrophages freshly obtained from rabbits, and the mixed composition cultured in a $CO_2$ incubator at 37° C. in a humidified atmosphere for between 24 and 72 hours, at least one multinucleated giant macrophage cell containing in excess of five nuclei will have formed; and examining the reaction of said lymphocyte sample and said antigenic tumor-specific substances and comparing said reaction with the reaction of said antigenic tumor-specific substances which have been contacted with a sample of viable lymphocytes from a host free from cancer, whereby when there is a difference in said two reactions, it is indicative that the lymphocyte sample taken from the host being tested is sensitized to cancer of the pathohistologic type as the cancer cells from which the antigenic tumor-specific substances were obtained.

2. The process of claim 1, wherein said lymphocyte sample taken from the host being tested is contacted with said antigenic tumor-specific substances in the presence of macrophages, and determining whether macrophage fusion has occurred to produce multinucleated giant macrophage cells whereby if said fusion has occurred, it is indicative that the lymphocytes in the sample were in a sensitized state to cancer indicating that the host from which they were extracted presently has or in the past had cancer of the pathohistologic type as the cancer cells from which the antigenic tumor-specific substances were obtained.

3. The process of claim 1, wherein said lymphocyte sample is contacted with said antigenic tumor-specific substances in the presence of a DNA-RNA reagent to determine the DNA-RNA proportion in the lymphocytes and comparing said value with a control lymphocyte sample, whereby if the sample being tested contains a proportion different from normal, that is, different from that in the non-cancer sensitized control sample, it is indicative that the said lymphocytes were sensitized by cancer indicating that the host from whom they were extracted presently has or in the past had cancer of the pathohistologic type as the cancer cells from which the antigenic tumor-specific substances were obtained.

* * * * *